United States Patent [19]
Liu et al.

[11] Patent Number: 6,099,473
[45] Date of Patent: Aug. 8, 2000

[54] METHOD AND APPARATUS FOR ANALYZING AN ULTRASONIC IMAGE OF A CARCASS

[75] Inventors: Yujun Liu, Chapel Hill, N.C.; James R. Stouffer, Ithaca, N.Y.; Greg Snider, Kearney, Nebr.

[73] Assignee: Animal Ultrasound Services, Inc., Ithaca, N.Y.

[21] Appl. No.: 09/245,181

[22] Filed: Feb. 5, 1999

[51] Int. Cl.$^7$ .......................................................... A61B 8/00
[52] U.S. Cl. .......................... 600/449; 600/443; 382/110; 73/602
[58] Field of Search .................................... 382/110, 194, 382/195; 600/443, 449, 447, 437; 73/602

[56] References Cited

U.S. PATENT DOCUMENTS

| | | | |
|---|---|---|---|
| 4,931,933 | 6/1990 | Chen et al. | 364/409 |
| 5,079,951 | 1/1992 | Raymond et al. | 73/602 |
| 5,208,747 | 5/1993 | Wilson et al. | 600/443 X |
| 5,339,815 | 8/1994 | Liu et al. | 128/660.01 |
| 5,944,598 | 8/1999 | Tong et al. | 452/158 |
| 5,960,105 | 9/1999 | Brethous | 382/141 |

*Primary Examiner*—Francis J. Jaworski
*Attorney, Agent, or Firm*—Brown, Pinnisi & Michaels

[57] ABSTRACT

The present disclosure teaches a system for analyzing ultrasonic image that provides an output of a measurement of muscle width from an ultrasonic image input of an outline of a muscle from an animal or carcass. The muscle that is used in the preferred embodiment is the longissimus dorsi muscle when an ultrasonic scan is taken in a transverse direction relative to the backbone. The analysis is done with a computer that receives the electronic input of rows and columns of gray level pixel data from an ultrasonic scan image of the outline of the muscle of the animal or carcass. The software is set to select a region of the ultrasonic image input to analyze to determine a first edge of the muscle. The selected region is divided into subregions $S_{j,k}$. J designates a row and ranges between 1 and n. K designates a column and ranges between 1 and o such that o is greater than 1. The subregions are aligned in rows and columns throughout the ultrasonic image input. The software calculates a sum of the gray level pixel data for each of the subregions $S_{j,k}$ then compares the sums to determine which of the subregions $S_{j,k}$ has the highest sum within each row j. The software defines a position of the first edge of the muscle by comparing the highest sum within each row j. This position is then used to calculate a relative muscle width when compared to a defined second edge of the muscle. The second edge can be defined as one edge of the selected region of the ultrasonic image input or it can be defined using the same steps used to define the first edge.

14 Claims, 3 Drawing Sheets

METHOD AND APPARATUS FOR ANALYZING AN ULTRASONIC IMAGE OF A CARCASS

FIELD OF THE INVENTION

The invention pertains to the field of ultrasonic animal and carcass evaluation, and more particularly relates to analyzing an ultrasonic image of an animal or carcass.

BACKGROUND OF THE INVENTION

Evaluating and grading meat animals, both live and slaughtered, has historically been performed by humans. Because of this it is very difficult to achieve accuracy, efficiency and consistency. Both producers and packers demand an objective means of classifying their animals accurately according to their carcass real values. However, since an accurate, quick, and consistent grading system has not been put into place, producers are not being paid for the true value of their animals. Currently, producers are paid on an average basis. The price differential between a high-yield and a low-yield grade is less than it should be. Therefore, it is important to the hog and beef industries that improved or new technologies must be developed in their evaluation systems in order to be able to accurately measure the hog and beef carcass characteristics that are of significant value.

Labor costs and inconsistent grading are significant problems in the meat processing industry. Attempts have been made to automate the grading and inspection systems involved in meat processing. For example see U.S. Pat. No. 4,931,933, entitled, "Application of Knowledge-Based System for Grading Meat" granted to Chen et al, and U.S. Pat. No. 5,079,951, entitled "Ultrasonic Carcass Inspection" granted to Raymond et al. However, these systems are overly complicated and do not provide an efficient method of accurately measuring the Longissimus dorsi muscle depth and fat composition.

The Longissimus dorsi muscle is one of the most valuable portions of beef or pork and is also an excellent indication of the value of the rest of the animal or carcass. Therefore, most analysis of animals or carcasses with ultrasound concentrates on this muscle.

Ultrasonic images of the Longissimus dorsi (rib eye muscle in beef and loin eye muscle in hogs) have been used to evaluate livestock. U.S. Pat. No. 5,339,815 (Liu et al.) discloses a method and apparatus wherein an ultrasonic transducer is centered in a longitudinal direction over the last few ribs of the animal or carcass and the ultrasonic image is of a ribline, a Longissimus dorsi muscle and fat layers above the muscle such that the specified window starts below the ribline of the animal or carcass. A fat depth is determined from a distance between the second interface line and a specified plane of contact between the animal or carcass and the ultrasonic transducer adjusted for any positioning equipment or stand-off gel. A muscle depth is determined from a distance between the first and second interfaces line. The output of the system includes the fat depth and the muscle depth for the animal or carcass from which the image was taken.

Longissimus dorsi or ribeye muscle cross-sectional area is currently obtained by manually tracing around the perceived outline of the muscle from an ultrasonic image. Some ultrasonic scanners, like the latest model we have been using [Aloka, 1990a], provide the capability of approximating the area with an ellipse. Due to its low degree of accuracy and the relatively large time requirement, this feature is seldom used. It is, however, more common for the images to be recorded on a video tape and the area analysis done at a later time. This analysis is still a very time consuming process. Because of the quality of the image, accurately tracing the l.d. muscle area can be done only by trained technicians. It is, therefore, very difficult to achieve efficiency, consistency and accuracy. The teachings of U.S. Pat. No. 5, 339,815 provided a method to automatically determine the area of the muscle when the ultrasonic scan image input is transverse with respect to a backbone of the animal or carcass. However, there are faster and easier methods for measuring the width of the muscle.

SUMMARY OF THE INVENTION

The present invention teaches a system for analyzing ultrasonic image that provides an output of a measurement of muscle width from an ultrasonic image input of an outline of a muscle from an animal or carcass. The muscle that is used in the preferred embodiment is the longissimus dorsi muscle when an ultrasonic scan is taken in a transverse direction relative to the backbone. The analysis is done with a computer that receives the electronic input of rows and columns of gray level pixel data from an ultrasonic scan image of the outline of the muscle of the animal or carcass.

The software is set to select a region of the ultrasonic image input to analyze to determine a first edge of the muscle. The selected region is divided into subregions $Sj_{,k}$. J designates a row and ranges between 1 and n. K designates a column and ranges between 1 and o such that o is greater than 1. The subregions are aligned in rows and columns throughout the ultrasonic image input. The software calculates a sum of the gray level pixel data for each of the subregions $Sj,k$ then compares the sums to determine which of the subregions $Sj,k$ has the highest sum within each row j. The software defines a position of the first edge of the muscle by comparing the highest sum within each row j. This position is then used to calculate a relative muscle width when compared to a defined second edge of the muscle. The second edge can be defined as one edge of the selected region of the ultrasonic image input or it can be defined using the same steps used to define the first edge.

The system is intended to be used in combination with a system for determining relative muscle depth. When used in combination the system can calculate a relative muscle area from the relative muscle width and relative muscle depth. Furthermore, the system can compare the relative muscle area to a measured weight of the animal or carcass and assign a relative value for use in further production of the animal or processing of the carcass.

DESCRIPTION OF THE PREFERRED EMBODIMENT

Figure 1:
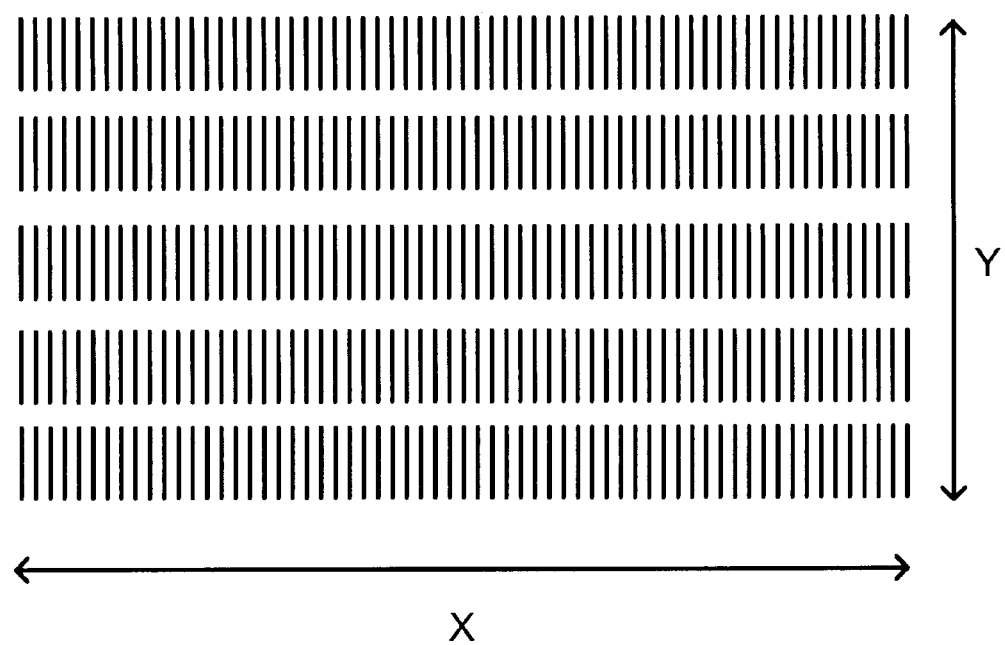
FIG. 1 shows a representative selected region of an ultrasonic image for analysis.

Several computer algorithms have been developed for subcutaneous fat thickness, longissimus dorsi muscle area, and intramuscular fat or marbling measurements from ultrasonic images of live animal and carcasses. The applicant's have previously developed a method of automatically determining the depth of the longissmus dorsi muscle in an ultrasonic image and were granted U.S. Pat. No. 5,339,815 for this system. The teachings of this patent is incorporated herein by reference. The present invention expands upon the teachings of this patent by teaching a method of determining a relative width of the longissimus dorsi muscle area in an ultrasonic image.

The invention disclosed in U.S. Pat. No. 5,339,815 (Liu et al.), incorporated herein by reference, introduces an automated system for ultrasonic carcass evaluation that uses the disclosed sliding z test for depth measurement and then measures the width of the muscle as set forth below. In essence, there is a difference in the ultrasound images of the muscle and the tissue adjacent the muscle. For determining the depth of the muscle, the edge detection technique involves finding the region where the difference between neighboring pixels reaches the computed threshold. The threshold is computed based on mean difference and standard deviation. This technique for determining the muscle depth always finds the region with a large gray value change that may not be the brightest spot.

For determining the width, the edge detection technique is to search the region with the highest average of gray values. The brightest area in average is found, which represents the interface between the muscle and surrounding tissue.

For this application, the term "AutoD" refers to the implementation of the technique disclosed in the '815 patent. The term "AutoW" refers to the implementation of the technique which is the subject of the present disclosure.

The present invention can be used in a variety of embodiments. In the way of example, the study of the longissimus dorsi muscle of swine is discussed herein. The characteristics of this muscle are currently the most important in determining the value of an animal or carcass. Specifically, the longitudinal images with respect to backbone of the animal or carcass are used in evaluation. Various positioning devices can assist in proper and consistent positioning of the ultrasonic transducer.

The Depth Measurement

Various edge detection algorithms for processing images have been developed, and most of them are typically modeled to detect a step edge in some optimal way. Detecting ideal step edges is a simple process. In real images, however, noise corrupts the edges and thus makes the edge detection a rather complicated process.

The AutoD system uses a process of measuring the distance between two detected boundaries and applies this technique as a method for on-line high speed evaluation of fat thickness in animal carcasses. Computational efficiency, therefore, is the major concern in developing the technique. A The one-dimensional sliding Z-test algorithm is used for the AutoD portion of the present invention for both edge and peak detection for the depth component. This algorithm requires the standard deviation of the whole area of interest in an image to be calculated only once. It not only simplifies the problem of edge detection but it is also very computationally efficient.

A brief description of Z-test will be given, followed by the description of edge detector and derivations of its expected value and variance together with analyses and determination of the unknown parameters. Finally the results of applying this technique to a set of ultrasonic images and the summary are presented.

Z-test The Z-test [Snedecor and Cochran, 1982] is based upon standard normal distribution which is completely determined by its mean $\mu$ and standard deviation $\sigma$. Any normally distributed variable X can be standardized to be a new variable Z with its mean equal to zero and standard deviation equal to one by the following simple formula, $$Z = \frac{X - \mu}{\sigma}. \qquad 1$$

The quantity Z is called standard normal deviate. The Z-test is performed simply by computing the Z value and testing it against its corresponding cumulative normal probability.

The most important features about the normal Z-test are that a population or a sampled population has its unique $\mu$ and $\sigma$, and that the distribution of a sample mean from it tends to become normal under random sampling as the size of sample increases even if the distribution in the original population is not normal, as illustrated by the central limit theorem [Mood et al., 1974]. The Sigma filter [Lee, 1983], which is used as a smoothing technique for image noise, is based on the normal probability distribution. Davis and Mitiche [1980] have developed image texture models for minimum error edge detection with an edge operator that is also assumed to be normally distributed.

Sliding Z-test Sliding Z-test, a new one-dimensional edge and peak detector based on Z-test, is presented. A one-dimensional edge detector in textures and reasons for considering a one-dimensional edge detector have been discussed [Davis and Mitiche, 1980].

A one-dimensional edge detector is based on differences of averages between adjacent, symmetric one-dimensional image neighborhoods. Consider a line of 2n pixels with its center denoted as location i. Let $x_1, x_2, \ldots, x_n$ denote gray levels of the first n pixel gray values, $y_1, y_2, \ldots, y_n$ denote gray levels of the next n pixel gray values in the line image; and denote their respective means. Then the magnitude of the edge operator is defined as $$d_i = \bar{x} - \bar{y} = \frac{\sum_{j=1}^{n} x_j}{n} - \frac{\sum_{j=1}^{n} y_j}{n}. \qquad 2$$

Our null hypothesis is that the sample values for any two adjacent neighborhoods come from the same normal distribution. Obviously it will be rejected if point i is at or near an edge. Under this hypothesis, sliding Z-test procedure involves the following three steps in detecting edges, in which $E[d_i]$ and $\sigma[d_i]$ denote the expected mean and standard deviation of $d_i$, respectively:

(1) Compute $Z_i = |d_i - E[d_i]|/\sigma[d_i]$ for all points i in the one-dimensional profile.

(2) Ignore location i where $Z_i < t$, The value t is a significant thresholding value which needs to be decided.

(3) Ignore location i where $Z_i < Z_{i+j}$, $j = \pm 1$.

Step 2, the thresholding step, is intended to discriminate between points which are edges or close to edges and points which are far from edges. Step 3, the non-maxima suppression step, is intended to discriminate between points which are edges and points which are close to edges. Since $d_i$ is large not only at edges but also near edges, omitting Step 3 would result in a cluster of detections about each true edge point [Davis and Mitiche, 1980].

Performing this edge detection procedure involves computing the expected mean, $E[d_i]$, and variance, $\sigma^2[d_i]$, of $d_i$ and choosing n and t in such a way that the overall probability of erroneously classifying an interior point as an edge point ($E_1$) or an edge point as an interior point ($E_2$) is minimal. A minimum error thresholding procedure can be found elsewhere [Davis and Mitiche, 1980; Gonzalez and Wintz, 1987].

It is worth noting that computation of the sliding Z-test can be carried out very efficiently by noting that $$d_{i+1} = d_i - \frac{x_1 - 2y_1 + y_{n+1}}{n}. \qquad 3$$

This indicates that $d_i$ can be computed in a constant number of operations per pixel, independent of n.

Analysis of edge magnitude $d_i$ For simplicity, suppose that the area of interest (AOI) in an image contains only two principal brightness regions: one for the dark regions corresponding to the background and one for the light regions corresponding to the bright boundary bands in the AOI. In this case the AOI is the sum or mixture of the two unimodel densities, whose brightness level is proportional to the brightness levels of the two principal regions. If a prior probability of one of the two regions is known or assumed, then the AOI overall average brightness level ($\mu_o$) is given by $$\mu_o = P_1\mu_2 + P_2\mu_2, \qquad 4$$

where $\mu_1$ and $\mu_2$ are the mean values of the dark and light regions with $\mu_2 > \mu_1$, and $P_1$ and $P_2$ are the prior probabilities of the dark and light regions, respectively, with the constraint $P_1 + P_2 = 1$. The overall variance σ about the mean $\mu_o$ in the AOI is $$\sigma_o^2 = Var(f_i - \mu_o) = Var(f_i - P_1\mu_1 - P_2\mu_2), \qquad 5$$

where $f_i$ is the gray level at pixel i, i=1, 2, . . . , N, with N indicating the total points in the AOI. After rearrangement and simplification with Equation 4, Equation 5 becomes $$\sigma_o^2 = P_1\sigma_1^2 + P_2\sigma_2^2 + \frac{P_1}{P_2}(\mu_o - \mu_1)^2, \qquad 6$$

where σ and σ are the variance about the means $\mu_1$ and $\mu_2$, respectively. In the following section for deriving the variance of $d_i$, it is assumed that the variances of the two principal regions are identical, denoted by the common variance $\sigma_2$, i.e., σ=σ=$\sigma^2$. Thus, with $P_1 + P_2 = 1$, $$\sigma_o^2 = \sigma^2 + \frac{P_1}{P_2}(\mu_o - \mu_1)^2, \qquad 7$$

If the identical variance assumption is not appropriate, the slope model with F statistic [Haralick, 1980] might be one of the alternatives. In the following sections the expected value and the variance of $d_i$ will be derived and $d_i$ will be expressed in terms of $P_1$, $P_2$, σ and simple correlations of neighboring pixels.

The Expected Value of d $E[d_i]$ By definition, the expected value of $d_i$ is $$E[d_i] = E[\bar{x} - \bar{y}] \qquad 8$$

-continued $$= E\left[\frac{\sum_{j=1}^{n} x_j}{n} - \frac{\sum_{j=1}^{n} y_j}{n}\right]$$

$$= \frac{1}{n}\left(\sum_{j=1}^{n} E[x_j]\right).$$

Under the null hypothesis that $x_j$ and $y_j$, j=1,2, . . . ,n, are drawn from the same distribution (either the dark regions or the light regions), the expected values are all the same, and thus $E[x_j] = E[y_j]$, j=1, 2, . . . , n for all points in that region. Therefore E[$d_i$| i is in the dark or light region]=0. Now if all or part of $x_j$ and/or $y_j$, j=1, 2, . . . , n, are drawn from the different distributions (cross the dark and light regions) and thus i is an edge or near edge point, then the expected value of $x_j$ and $y_j$ may or may not be equal, depending upon the size of n and the pattern distributions of the dark region and the light region. Hence, |E[$d_i$| i is an edge or near edge point]|≧0. Davis and Mitiche [1980] should be consulted for an exact solution of E[$d_i$] given i is an edge or near edge point. But to be consistent with the null hypothesis, taking the expected value of $d_i$ as 0 would not be invalid particularly for the view of image processing since any $d_i$ significantly different from 0 would be of interest and should be detected by the sliding Z-test. Therefore, it will be assumed under the null hypothesis that E[$d_i$]=0 for i=1, 2, . . . , N.

The Variance of $d_i$, $\sigma^2[d_i]$ The variance of $d_i$ is given by:

$$\sigma^2[d_i] = Var[d_i]$$

$$= Var[\bar{x} - \bar{y}]$$

$$= \sigma^2[\bar{x}] + \sigma^2[\bar{y}] - 2\tau_{x,y}\sigma[\bar{x}]\sigma[\bar{y}]. \qquad 9$$

where τ, is the correlation between and . It is not assumed that the adjacent neighborhoods are independent. If they are independent, τ, would be 0. Under the null hypothesis, $\sigma^2$[x bar]=$\sigma^2$[y bar]. Denoted by a common variance $\sigma^2$[g bar], Equation 9 becomes $$\sigma^2[d_i] = 2(1 - \tau_{\bar{x},\bar{y}})\sigma^2[\bar{g}], \qquad 10$$

$$\bar{g} = \frac{1}{n}\sum_{j=1}^{n} f_j. \qquad 11$$

Under the null hypothesis, the variance of $d_i$ given by Equation 10 is the variance for all i, i=1, 2, . . . , N.

From Equation 11, the variance of g bar, $\sigma^2$[g bar], can be derived in terms of simple correlations of neighboring pixels and the common variance $\sigma^2$ of the two principal regions.

$$\sigma^\dagger[\bar{g}] = Var\left(\frac{\sum_{j=1}^{n} f_j}{n}\right) \qquad 12$$

$$= \frac{Var\left(\sum_{j=1}^{n} f_j\right)}{n^\dagger}$$

-continued $$= \left(\frac{1}{n} + \frac{2\sum_{j=1}^{n-1}\sum_{k=1}^{n-j}\tau_{j,j+k}}{n^\dagger}\right)\sigma^\dagger,$$

where $\tau_{jj+k}$ is the correlation between pixel j and pixel j+k. There are n!/2 possible correlations, $\Sigma_{jj+k}$, involved to compute the variance of without the assumption of neighborhood independence. For simplicity, it is reasonable to assume that the correlation of two pixels in a fixed distance is invariant for a particular set of images. Mathematically speaking, it is assumed that $\tau_{1,1+k}$ is equal to $\tau_{jj+k}$ for any j and k (j=1, 2, ..., n-k; k=1, 2, ... n-1) with $\tau_{1,1+k}$ representing the correlation between a pixel and its kth neighbor. By letting $\rho_k$ denote $\tau_{1,1+k}$, it can be established that there will be n-1 $\rho_1$'s, n-2 $\rho_2$'s, ..., and one $\Sigma_{n-1}$. This assumption, consequently, reduces the number of possible correlations among the n points from n!/2 to n-1. Hence the variance of g bar, $\sigma^2$[g bar], is given by:

$$\sigma^\dagger[\bar{g}] = \left(\frac{1}{n} + \frac{2\sum_{j=1}^{n-1}(n-j)\rho_j}{n^\dagger}\right)\sigma^\dagger. \qquad 13$$

It can also be shown that the correlation between the averages of adjacent, symmetric neighborhoods and is a function of the simple correlations between the 2n pixels involved in and.

$$\tau_{\bar{x},\bar{y}} = \frac{\sum_{j=1}^{n}j\rho_j + \sum_{j=1}^{n-1}(n-j)\rho_{n+j}}{n + 2\sum_{j=1}^{n-1}(n-j)\rho_j}. \qquad 14$$

These correlations of neighboring pixels must be established either theoretically or experimentally. Because of the complexities and diversities associated with digital images, most statistical models of image noise assume that the noise intensity between pixels is not correlated. The neighborhood correlations will be determined experimentally in the next section.

The common variance $\sigma^2$ of the two principal regions in Equation 13 is an unknown parameter. At the beginning of this section, the overall variance $\sigma$ has been partitioned into two parts in Equation 7. The difference $\mu_o - \mu_1$ in Equation 7 can be approximated by using the optimal thresholding technique [Gonzalez and Wintz, 1987] to solve $\sigma^2$. From the definitions of $\mu_o$, $\mu_1$ and $\mu_2$ and Equation 4, it can be shown that $\mu_1 < \mu_o < \mu_2$ and that $$\mu_2 - \mu_1 = \frac{\mu_o - \mu_1}{P_2}. \qquad 15$$

Thus a threshold T may be defined so that all pixels with a gray value below T are considered dark points and all pixels with a value above T are consider light points. Based on the minimal error thresholding formula in [Gonzalez and Wintz, 1987] with identical variance $\sigma^2$ for the two regions, the optimal solution for T is $$T = \frac{\mu_1 + \mu_2}{2} + \frac{\sigma^2}{\mu_1 - \mu_2}\ln\left(\frac{P_2}{P_1}\right). \qquad 16$$

Furthermore, suppose that T is $Z_o$ normal deviates greater than $\mu_1$, based on the concept of statistical significant test, that is, $$T = \mu_1 + Z_o\sigma. \qquad 17$$

Combining Equations 15, 16 and 17 with rearrangement and simplification yields the following:

$$\mu_o - \mu_1 = P_2\left(Z_0 + \sqrt{Z_0^2 + 2\ln\left(\frac{P_2}{P_1}\right)}\right)\sigma \qquad 18$$
$$= C\sigma,$$

where $$C = P_2\left(Z_0 + \sqrt{Z_0^2 + 2\ln\left(\frac{P_2}{P_1}\right)}\right). \qquad 19$$

Replacing $\mu_o - \mu_1$ with $C\sigma$ and solving for $\sigma^2$ from $\sigma$ in Equation 7 finally give $$\sigma^2 = \frac{\sigma_o^2}{\left(1 + C^2\frac{P_1}{P_2}\right)}. \qquad 20$$

By joining Equations 13, 14 and 20, the variance of $d_1$, $\sigma^2[d_i]$, in Equation 10 can be expressed as a function of $P_1$, $P_2$, $\sigma$, $Z_o$, and 2n-1 neighborhood correlations under the null hypothesis. In order to detect edges using the sliding Z-test as proposed above it is necessary to:

1. determine the prior probabilities of dark and light points $P_1$ and $P_2$;
2. specify significant normal deviates $Z_o$ and t;
3. choose the size of sliding window 2n;
4. check 2n-1 neighborhood correlations; and
5. compute $\sigma$ in the area of interest of an image.

Estimation of Unknown Parameters Unknown parameters ($P_1$ and $P_2$, $Z_o$ and t, n, $\rho_i$ with i=1, 2, ..., 2n-1) involved in the above sections depend upon the application and the characteristics of a particular kind of images. Hence there is no single solution to all different images. The following methods are suggested to estimate the unknowns.

In determination of the probabilities $P_1$ and $P_2$ in general, it is hoped ideally that based on the definition of the optimal thresholding value T, the probability of a point $f_i$, i=1, 2, . . ., N, in the dark regions ($P_1$) or in the light regions ($P_2$) are $P_1 = P\{f_i \leq T\}$ and $P_2 = 1 - P_1$ with the assumption that the probability of erroneously classifying either an interior point as an edge point ($E_1$) or an edge point as an interior point ($E_2$) is negligible. In other words, if either the total points with $f_i \leq T$, denoted by $N_1$, or the total points with $f_i > T$, denoted by $N_2$, is known with $N_1 + N_2 = N$, then $P_1$ and $P_2$ can be estimated as follows: $P_1 \approx N_1/N$ and $P_2 \approx N_2/N$. For instance, in characterizing ultrasonic images from animal loin cross section scans for tissue linear measurements, $N_2$ may be estimated by the number of tissue boundaries (b) involved in the area of interest which appear bright in the ultrasonic image and the width of each (represented by wk, k=1, 2, . . . , b), that is, $$N_2 = \sum_{k=1}^{b} w_k. \qquad (21)$$

In determining the value of n, the minimum of $W_k$, k=1, 2, ..., b, is chosen, based on both the findings of [Davis and Mitiche, 1980] and the consideration of reserving the characteristics of an edge. Symbolically, n=min{wk, k=1, 2, ..., b}. An n too small or too large will increase the probability of error $E_1$ or $E_2$ [Davis and Mitiche, 1980]. By a careful examination of several images used in the discovery of the present invention, it was found that n less than 3 or greater than 10 did not work well for fat depth measurements since most boundary bands were averaged 5 pixels wide in those images. The standard normal deviates $Z_o$ for optimal thresholding and t for sliding Z-test process can be determined based on normal distribution. $Z_o$=t=3 has been used with a great success in several sets of animal ultrasonic images. This value is recommended since it means that 99.87% of points in the AOI of an image would be correctly classified and that with non-maxima depression step (Step 3 in Sliding Z-test) this probability should be even higher.

As mentioned earlier, speckle noise such as that of ultrasound can not be presumed statistically independent [Burckhardt, 1978]. One simple method to determine the independence is to compare the correlation coefficients [Lee, 1981]. Correlations of neighboring pixels in an image could be determined based on individual images by adopting the formula given in [Lee, 1981]. The $r_{0,1}$ is the correlation coefficient of a pixel and its immediate right neighbor. The $r_{k,0}$ is the estimate of $\rho_k$, k=1, 2, ..., when the sliding Z-test is used to detect vertical edges while the $r_{0,k}$ is the estimate of $\rho_k$, k=1, 2, ..., when the sliding Z-test is used to detect horizontal edges. The results indicate that pixels have high correlations with their neighbors and the correlations decrease with pixels farther away. More than 20 images with the same size of window have been tested and the results are similar to the above. Hence it may be reasonable to assume that the correlation between two pixels of a fixed distance is invariant for a particular set of images, independent of the region (either the light or dark region) in which it has been calculated. Making such an assumption will substantially save time on computation but it may not be valid for other images. It is interesting to note that vertical correlations are consistently lower than horizontal ones. This may be because the horizontally oriented, linearly arrayed elements of the transducer used herein [Aloka 1990a and 1990b] produce similar ultrasonic waves which attenuate differently, while travelling in the direction normal to the transducer face, depending on the characteristics of the scanned materials.

When an input is provided of an ultrasonic scan image of the muscle and fat area of the animal or carcass comprising rows and columns of pixel data, a window of rows and columns of pixels within the image input is selected. The window includes a bottom and upper row of pixels.

Scanning downward, starting at as defined above within the window, an interface is determined. The sliding lower box of pixels and the adjacent sliding upper box of pixels are defined to move up through the window one row at a time at least until the interface is determined. The expected value and the standard deviation of the difference between the means of the gray levels of the pixels within the sliding lower box and the sliding upper box are calculated. A number of normal deviates value is calculated for each row of pixels moving upwards through the window, wherein the number of normal deviates value is computed by dividing the absolute value of the difference of the means of the gray levels of the pixels within the sliding lower box and the upper box less the computed expected value, by the computed standard deviation. The interface is defined at a specified row of pixels when the number of normal deviates value for the specified row of pixels is greater than both a predefined interface threshold and is greater than the number of normal deviates value calculated for the row of pixels one row lower and one row higher than the specified row of pixels. If any of these criterion are not met then the process proceeds from one row higher. Otherwise the interface has been determined. A second interface can be determined by scanning upward through the window beginning at a point above the determined first interface. Then an output of the determined interfaces and is provided. The method can assume that the expected value of the difference between the means of the gray levels of the pixels within the sliding lower box and the sliding upper box equal zero and that the standard deviation of the means of the gray levels of the pixels within the sliding lower box and the sliding upper box are equal.

The method has been used to locate interfaces when wherein an ultrasonic transducer was centered over the last few ribs of the animal or carcass and the ultrasonic image is of a ribline a longissimus dorsi muscle and fat layers above the muscle such that the specified window starts below the ribline of the animal or carcass. A fat depth was determined from a distance between the second interface line and a specified plane of contact between the animal or carcass and the ultrasonic transducer adjusted for any positioning equipment or stand-off gel. A muscle depth was determined from a distance between the first and second interfaces lines. The output of the system included the fat depth and the muscle depth for the animal or carcass from which the image was taken. The method can be used when the ultrasonic scan image input is either longitudinal or transverse with respect to a backbone of the animal or carcass.

The area of interest in the image was specified according to the conventional location for fat measurements in swine and beef, which was approximately at the 50th row and 232nd column for its upper left corner and the 219th row and 271st column for its lower right corner in the image, giving N=170×40. The 170 rows in depth was large enough to cover all possible subcutaneous-fat-tissue-involved interfaces interested in the images. The sliding Z-test was to cross these rows to detect edges in the images.

Since this technique is one-dimensional, any box width greater than one column is for making multiple measurements. How wide the area should be depends primarily upon the quality of the image as well as a particular application.

The width of 40 columns was used for transverse images based on the fact that some noise and artifacts could be as wide as 20 columns (most often 2 to 8 columns wide) in those images. Of these 40 columns 10 measurements were made (one every 4 columns) and the 2 highest and 2 lowest values were eliminated. The remaining measurements were averaged and this average was used to compare with its corresponding manual measurement. This edge detection procedure is now used to detect interfaces in longitudinally scanned images with amazing success. When using this technique in longitudinal scans multiple measurements could be made across the image.

In order to estimate the unknown parameters involved in the sliding Z-test algorithm, it is necessary to consider the following possible interfaces among the ultrasonic transducer and the underneath tissues in swine, which appear bright in the ultrasonic image. There are three visible fat layer in swine images but only two visible fat layers in beef images. The average width of each bright interface band was determined based on the histogram analyses of more than 20 various images. The minimum of these widths, 3, was the number of pixels used to compute the average in each side of the sliding window. $Z_o=t=3$, the standard normal deviates, was used based on normal distribution assumption.

The conversion factors from row pixels to centimeters are transducer dependent, which can be easily determined from the scales shown on the image. For transducer UST-501 IU-3.5 MHz, one cm is equivalent to 30.20 rows and for transducer UST-5044U-3.5 MHz, one cm is equivalent to 22.20 rows.

The Width Measurement

AutoD has proven to be an extremely useful tool in evaluating carcasses and livestock. In an expansion of this utility a method of automatically determining the width of the muscle was developed. The automatic width method (AutoW) searches for the left or right end of the muscle from an ultrasonic image. It assumes that there is an interface at the end of the muscle which produces the brightest image.

The ultrasonic image is composed of rows and columns of pixels that are have a particular grey value. The higher the grey value the "brighter" the image for a particular pixel. Generally speaking, evaluation of animals and carcasses is performed with transducers and ultrasound equipment that generate a rectangular image. The rectangular image includes the region of the muscle to be examined. Depending upon the application, a smaller portion of the total image may be selected for analysis.

In any event, the image, or a portion thereof, is selected for analysis is subdivided into smaller regions. Typically the selected region is divided into 5 equally spaced rows and a large number of columns about 3 pixels wide, as shown in FIG. 1, although each of these parameters can be changed by the user.

The following variables are used in the calculation:
a) Y=total height in pixels of the selected image region
b) X=total width in pixels of the selected image region
c) n=the number of rows (subregions) in the selected image region
d) m=the width in pixels of the subdivided region The image shown in FIG. 1 is Y pixels high and X pixels wide, such that the height of each subregion is Y/n. The value n is run-time defined with a default of 5. Changing n also affects the AutoD component of the invention.

For each subregion, the gray values of image pixels in m vertical lines (the default value of m is 3, the same default value used by AutoD) are summed up in a sliding fashion pixel by pixel from left to right. Each sum is from (m*Y/n) pixels. Therefore, there are (X/m) sums. The method is looking for the brightest spot as it "slides" from left to right along each of the rows. The position with the maximum of the sums (Xmax) is saved.

There is an Xmax for each of the n rows making up the sub regions. In total, there are n Xmax values, each from a subregion. A smoothed average of the n Xmax is assumed to be the end of the muscle. The smoothed average is runtime defined that is preferably one of the following:

1) Arithmetic average: (Xmax1+Xmax2+Xmaxn)/n
2) Median: Sort Xmax in order. The median is the middle value if n is odd and the average of middle two values if n is even.
3) Trimmed average: Sort Xmax in order and trim off the minimum and maximum.

The Trimmed average is the average of the remaining n−2 values.

The default method of calculating the smoothed average is Median. Changing the smoothed average can also affect AutoD. AutoW can be implemented with AutoD on or off, thereby affecting the size of the rectangular region of an image to search. All values are in pixels When AutoD is on, the automatic region bounded for searching the left end of the muscle is defined by Top: (The y location of the fat and muscle interface line)+10

Left: (The x location of the left end of the fat and muscle interface line)

Bottom: Top+(Muscle depth in pixels)/3

Right: Left+(The length of the fat and muscle interface line)/3

The automatic region bounded for searching the right end of the muscle is defined by Top: (The y location of the fat and muscle interface line)+10+(Muscle depth in pixels)/3

Left: (The x location of the left end of the fat and muscle interface line)+(The length of the fat and muscle interface line)/3*2

Bottom: Top+Muscle depth in pixels)/3 s

Right: Left+(The length of the fat and muscle Interface line)/3

When AutoD is off, the automatic region bounded for searching the left end of the muscle is defined by Top: 90

Left: 80

Bottom: Top+240/3=170

Right: Left+280/3=173

The automatic region bounded for searching the right end of the muscle is defined by Top: 90+240 3=170

Left: 80+280/3*2=266

Bottom: Top+240/3=250

Right: Left+280/3 =359

The pixel width measured by AutoW is the horizontal distance between the left and right ends of the muscle. This value is converted to the selected unit of measurement based on the probe calibration.

The analysis is done with a computer that receives the electronic input of rows and columns of gray level pixel data from an ultrasonic scan image of the outline of the muscle of the animal or carcass. The software is set to select a region of the ultrasonic image input to analyze to determine a first edge of the muscle. The selected region is divided into subregions $S_{j,k}$. J designates a row and ranges between 1 and n. K designates a column and ranges between 1 and o such that o is greater than 1. The subregions are aligned in rows and columns throughout the ultrasonic image input. The software calculates a sum of the gray level pixel data for each of the subregions Sj,k then compares the sums to determine which of the subregions Sj,k has the highest sum within each row j. The software defines a position of the first edge of the muscle by comparing the highest sum within each row j. This position is then used to calculate a relative muscle width when compared to a defined second edge of the muscle. The second edge can be defined as one edge of the selected region of the ultrasonic image input or it can be defined using the same steps used to define the first edge.

AutoW can be used either with AutoD or independently. When AutoW is activated in either case, the left or right side of an image is set to a fixed location if the parameter associated with that side is set to a non-negative value. There are six input parameters associated with AutoW:

1) Activate Check: When selected, AutoW is activated. When activated, AutoW will make a width measurement on an image after the image is capture or opened from a file. If AutoD is activated, AutoW will be made after AutoD. AutoW can be activated only if it is available and enabled.

2) Output Col: Enter a column code from A to IV (Default code is G). The AutoW measurement is in this column with 'aMW' as its default column heading. The user preferably can change any column heading to a more meaningful term.

3) Left: Enter any value from −511 to 511 in column pixels. When negative, AutoW searches for the left end of the image; otherwise, AutoW uses this value and sets it as the left end of the image. The default value is 76.

4) Right: Enter any value from −511 to 511 in column pixels, When negative, AutoW searches for the right end of the image; otherwise, AutoW uses this value and sets it as the right end of the image, The default value is −1.

5) Top: Enter any value from −479 to 479 in row pixels. When negative, AutoW searches within the AutoD muscle depth region if AutoD is activated and within rows from 80 to 240 if AutoD is not activated; otherwise, AutoW uses this value as its top and searches below it, The default value is −1.

6) Bottom: Enter any value from −479 to 479 in row pixels- When negative, AutoW searches within the AutoD muscle depth region if AutoD is activated and within rows from 80 to 240 if AutoD is not activated; otherwise, AutoW uses this value as its bottom and searches above it. The default value is −1.

Figure 3:
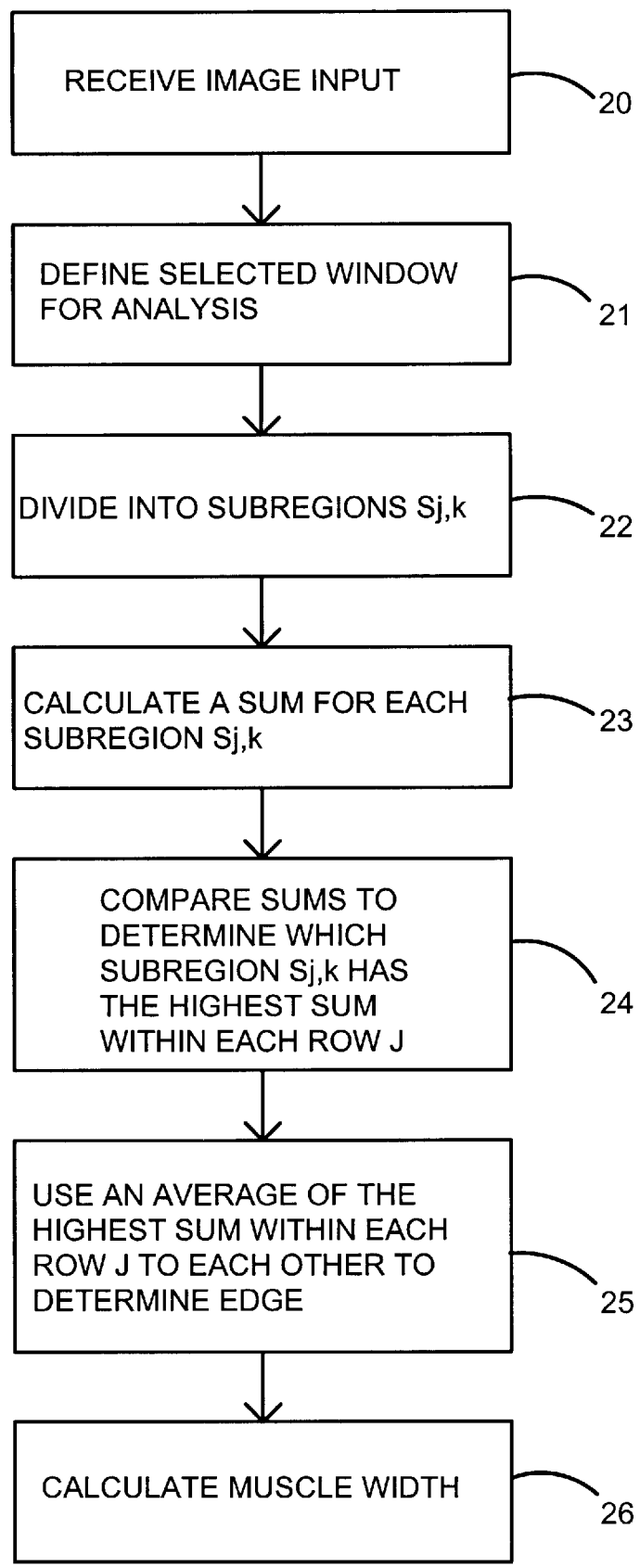
FIG. 3 is a flow chart of the basic steps for determining an interface within the image.

FIG. 3 is a flow chart of the basic steps to determining an interface within the image. An input is provided of an ultrasonic scan image of the muscle and fat area of the animal or carcass comprising rows and columns of pixel data. (Box 20) A window of rows and columns of pixels within the image input is selected. (Box 21) The window is divided into subregions (Box 22) both horizontally and vertically and the sums of each subregion is determined (Box 23). The max Sum for each subregion within a horizontal region is determined (Box 24). Then the position of the max Sum for each horizontal region is compared to the other horizontal regions (Box 25). Finally and an average of the max Sums is used to determine the position of the right side of the muscle (Box 26).

Application

Figure 2:
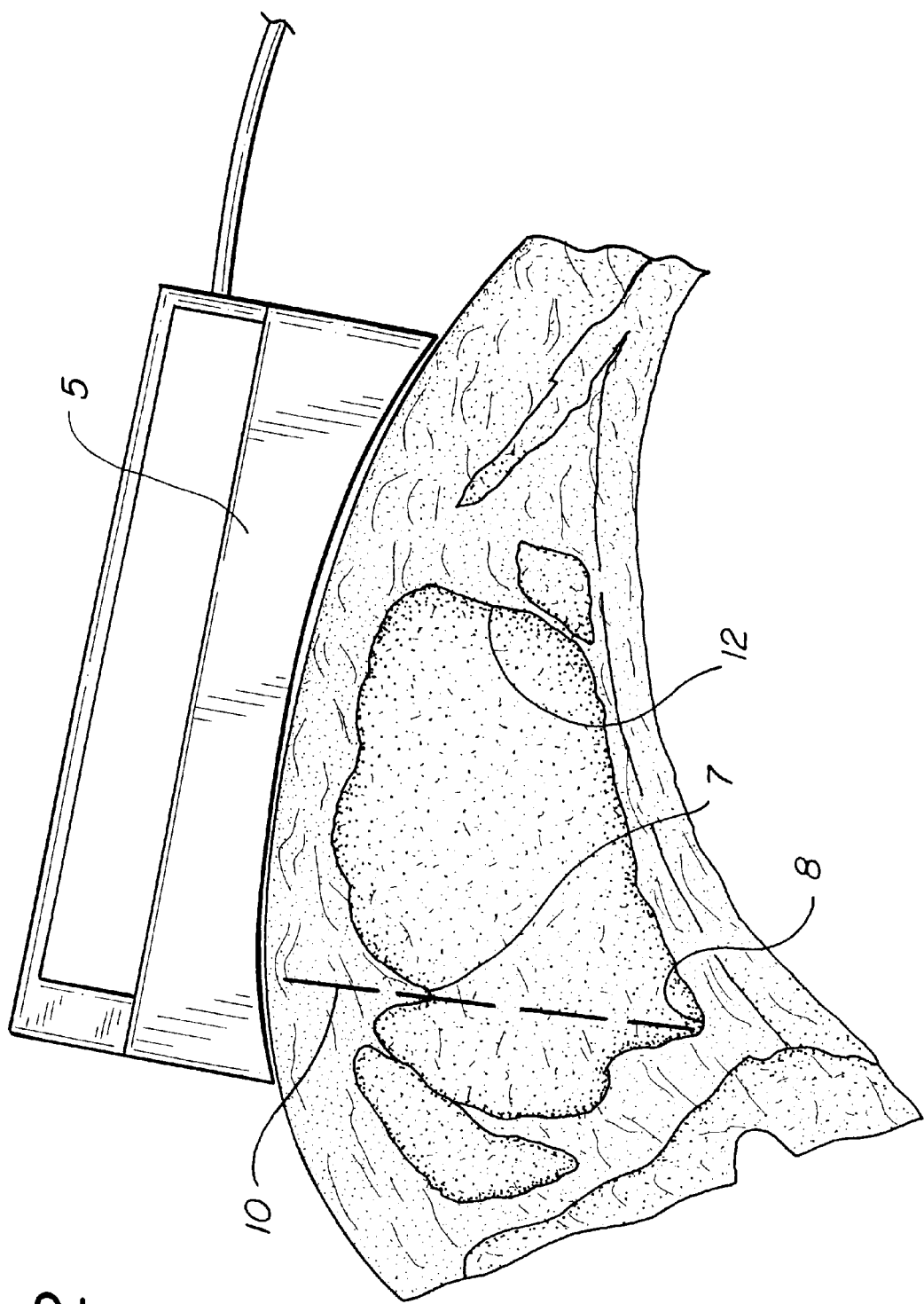
FIG. 2 shows a representation of an ultrasonic transducer positioned to scan a longissimus dorsi muscle, with a transducer positioned in a transverse direction with respect to an animal's backbone.

The present invention teaches a method of automatically recognizing fat and muscle interfaces of an animal or carcass from an ultrasonic image of a muscle and fat area. FIG. 2 shows a representation of the positioning of a transducer 5 in a transverse direction with respect to the animal's backbone, specifically a beef carcass. The transducer 5 is positioned such that the left side of the image runs through an indent 7 in the top of the l.d. muscle and continues through the bottom left corner of the muscle 8. The line between these two points are marked a cross hatched line 10.

From empirical study it has been determined that the proportion of the muscle to the left of the line is the same relative to the total muscle. Therefore, for speed in analysis and for consistent operation, the preferred embodiment is to have the user position the transducer such that the left side of the ultrasonic image starts along this line 10. Therefore, the width of the muscle measured by assuming that the left side of the ultrasonic image is the left side of the muscle and then determining the position right side of the muscle 12. This way the computer does not have to search for both sides of the muscle. This is true for both live animals and carcasses.

In addition, the area of the muscle is calculated by determining the area between the left side of the image, the right side of the muscle and the top and bottom of the muscle. This area is roughly a rectangle, but the muscle is slightly more elliptical in reality. This is also fairly consistent between animals and a standard proportion of the measured area is actually muscle.

The analysis can correct for this and the portion of the muscle to the left of the line 10, however, the importance of the invention is to provide an objective measurement that can be compared to the same measurement made in other carcasses or animals for determining a relative value. In other words, if the measurement is off by a certain percentage is does not matter so long as the measurement is off by that percentage for all measurements. The producers and processors are concerned about percent lean and relative size of the l.d. muscle when compared to the overall weight of the animal or carcass.

This invention may be used alone, but the preferred implementation is to use the AutoW in a combined system with AutoD and other ultrasound analysis tools (e.g. marbling or intra muscular fat analysis) for both live animal and carcass evaluation. Some processors are already using % lean as measured by AutoD to determine how much to pay producers.

The teachings of the present invention are efficient enough to be implemented in a real time system. The transducer can be positioned manually or automatically on carcasses or animals and then the images can be processed fast enough to allow real time evaluation and sorting. This is extremely important in a practical application of the present invention. Meat processors or breeders will be able to use the present system to sort animals or carcasses based upon the information provided. Such efficient sorting can result in a more profitable processing of carcasses in that only the more valuable carcasses will be selected to go through the more expensive processing steps. Breeders can efficiently select stock for breeding or slaughter based upon the information provided by the present system. Some practical hints for designing a real time system are provided herein, however, it is expected that when each of the many applications of the teachings of the present invention are implemented further features can be added by the user of the system.

The system can be built in such a way that it can automatically make the decision as to whether or not there is a valid image, regardless of the existence of an animal or carcass identification on the image. Freezing and releasing an image does not alter the previous inputs to the surrounding area including the ID field. This decision must also be made fast enough for near real-time operation since all the input information will be lost during the decision making period. Hence, the algorithm used for this purpose must be simple but efficient.

If the interval image between two animals or carcasses is black or very low in image intensity, compared with a normal ultrasonic image from a animal or carcass, then the image intensity can be used to verify whether or not there is a desired image. By analyzing the images, it was found that normal ultrasonic images had average gray values greater than 30, about 12% of the maximum intensity. Although the image intensity can be controlled by the machine operator, an image with intensity lower than 12% of the maximum is hardly visible. This is a very simple mechanism for image verification but either too low or too high a threshold selected may result in a loss of useful image.

The timing for triggering a measurement depends on both the software execution speed and the on site speed of a particular application. For instance, the chain speed of a large modem commercial abattoir can be as high as 1200 hogs or 400 beef per hour. This speed must be matched for practical application of an automated system in commercial slaughter houses. Suppose that one set of the automated system is used for hogs in a packing plant which operates at the chain speed of 1200 carcasses per hour, and that an operator or robot is able to correctly locate the ultrasonic transducer and to obtain a quality image from each hog carcass passed by. This means that, with the image source passed through the image grabber board, the system must be capable of digitizing an image and making all pre-specified measurements within 3 seconds for each hog (3600 seconds/1200 hogs).

Image Capture Hardware. The image capture hardware used for the verification of the teachings of the present invention included the Cortex-I and CX100 from ImageNation and a video digitizer PCMIA card from MRT Micro, Inc. of Del Ray Beach, Fla. Once the ultrasonic image is digitized using these image digitizing devices, the AutoD and AutoW analyses no longer depend on the image capture hardware.

Computer Hardware. The system used a portable 486 PC and a Pentium PC.

Software requirement. Microsoft Visual C++ ver. 1.5 was used to develop the AUSKey software. The final product is a stand-alone executable software package whose Windows version runs on Windows 3.1 or higher and whose DOS version runs on DOS 3.0 or higher.

Ultrasonic Equipment. The equipment used to acquire ultrasonic images from beef and swine was a real time ultrasonic scanner Aloka SSD-500V with 3.5 Mhz linear array transducers [Aloka, 1990a, 1990b and 1990c]. The images can be recorded in VHS video tapes with a regular video cassette recorder and then played back for processing. The video output on the ultrasonic unit will normally connect to the image grabber board for immediate processing in an permanent on-line operation.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method for providing a measurement of muscle width from an ultrasonic image of an outline of a muscle from an animal or carcass, comprising the following steps:
   a) providing computer having:
      1) a computer processor operatively connected to a storage device that is capable of storing control logic for said processor,
      2) an electronic input device operatively connected to said computer processor for receiving an input of rows and columns of gray level pixel data from an ultrasonic scan image including said outline of said muscle of said animal or carcass,
      3) first control logic that selects a region of said ultrasonic image input to analyze to determine a first edge of said muscle,
      4) second control logic that divides said selected region of said ultrasonic image input into subregions $S_{j,k}$, wherein j designates a row and ranges between 1 and n and wherein k designates a column and ranges between 1 and o such that o is greater than 1, such that said subregions are aligned in rows and columns throughout said ultrasonic image input,
      5) third control logic that calculates a sum of said gray level pixel data for each of said subregions $S_{j,k}$ within each row j,
      6) fourth control logic that compares said sums for each of said subregions $S_{j,k}$ to determine which of said subregions $S_{j,k}$ has the highest sum within each row j,
      7) fifth control logic that compares said subregions $S_{j,k}$ with the highest sum for each row j to define a position of said first edge of said muscle, and
      8) sixth control logic that uses said defined position of said first edge of said muscle to provide a measurement of a relative width of said muscle by comparing said defined position to a defined second edge of said muscle as output;
   b) providing an input of rows and columns of gray level pixel data of an ultrasonic scan image including said outline of said muscle of said animal or carcass to said computer system; and
   c) using said computer system to provide a measurement of a relative width of said muscle by comparing said defined position to a defined second edge of said muscle as output.

2. The method of claim 1, wherein said defined second edge is defined as one edge of said selected region of said ultrasonic image input.

3. The method of claim 1 wherein said defined second edge is defined using the same steps used to define said first edge.

4. The method of claim 1, wherein said muscle is a longissimus dorsi muscle and said ultrasonic image input is an ultrasonic image input of said longissimus dorsi muscle in a transverse direction with respect to a backbone of said animal or carcass.

5. The method of claim 1, wherein said method is used in combination with a method for determining relative muscle depth.

6. The method of claim 5, wherein a relative muscle area is calculated from said relative muscle width and relative muscle depth.

7. The method of claim 6, wherein said relative muscle area is compared to a measured weight of said animal or carcass and assigned a relative value for use in further production of said animal or processing of said carcass.

8. A system for analyzing ultrasonic image that provide an output of a measurement of muscle width from an ultrasonic image input of an outline of a muscle from an animal or carcass, comprising the following steps:
   a) a computer having a computer processor operatively connected to a storage device that is capable of storing control logic for said processor;
   b) an electronic input device operatively connected to said computer processor for receiving an input of rows and columns of gray level pixel data from an ultrasonic scan image including said outline of said muscle of said animal or carcass;
   c) first control logic that selects a region of said ultrasonic image input to analyze to determine a first edge of said muscle;

d) second control logic that divides said selected region of said ultrasonic image input into subregions $S_{j,k}$, wherein j designates a row and ranges between 1 and n and wherein k designates a column and ranges between 1 and o such that o is greater than 1, such that said subregions are aligned in rows and columns throughout said ultrasonic image input;

e) third control logic that calculates a sum of said gray level pixel data for each of said subregions $S_{j,k}$ within each row j;

f) fourth control logic that compares said sums for each of said subregions $S_{j,k}$ to determine which of said subregions $S_{j,k}$ has the highest sum within each row j;

g) fifth control logic that compares said subregions $S_{j,k}$ with the highest sum for each row j to define a position of said first edge of said muscle; and h) sixth control logic that uses said defined position of said first edge of said muscle to provide a measurement of a relative width of said muscle by comparing said defined position to a defined second edge of said muscle as output.

9. The system of claim 8 wherein said defined second edge is defined as one edge of said selected region of said ultrasonic image input.

10. The system of claim 8 wherein said defined second edge is defined using the same steps used to define said first edge.

11. The system of claim 8, wherein said muscle is a longissimus dorsi muscle and said ultrasonic image input is an ultrasonic image input of said longissimus dorsi muscle in a transverse direction with respect to a backbone of said animal or carcass.

12. The system of claim 8, wherein said system is used in combination with a system for determining relative muscle depth.

13. The system of claim 12, further comprising control logic that calculates a relative muscle area from said relative muscle width and relative muscle depth.

14. The system of claim 13, further comprising control logic that compares said relative muscle area to a measured weight of said animal or carcass and assigns a relative value for use in further production of said animal or processing of said carcass.

* * * * *